United States Patent
Hisamichi et al.

(10) Patent No.: US 6,797,706 B1
(45) Date of Patent: Sep. 28, 2004

(54) HETEROCYCLECARBOXAMIDE DERIVATIVE

(75) Inventors: Hiroyuki Hisamichi, Ibaraki (JP); Souichirou Kawazoe, Ibaraki (JP); Kazuhito Tanabe, Ibaraki (JP); Atsushi Ichikawa, Ibaraki (JP); Akiko Orita, Ibaraki (JP); Takayuki Suzuki, Ibaraki (JP); Kenichi Onda, Ibaraki (JP); Makoto Takeuchi, Ibaraki (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 138 days.

(21) Appl. No.: 10/009,276

(22) PCT Filed: Jun. 9, 2000

(86) PCT No.: PCT/JP00/03767

§ 371 (c)(1),
(2), (4) Date: Dec. 10, 2001

(87) PCT Pub. No.: WO00/75113

PCT Pub. Date: Dec. 14, 2000

(30) Foreign Application Priority Data

Jun. 9, 1999 (JP) ............................................. 11-162692

(51) Int. Cl.[7] .................... A61K 31/33; A61K 31/4965; C07D 241/00; C07D 241/02
(52) U.S. Cl. ............... 514/183; 514/252.1; 514/255.06; 544/224; 544/336; 544/406; 544/407
(58) Field of Search ............................. 514/183, 252.1, 514/255.06; 544/224, 336, 406, 407

(56) References Cited

U.S. PATENT DOCUMENTS 4,442,095 A * 4/1984 Johnston .................. 514/232.2

6,432,963 B1    8/2002   Hisamichi et al.

FOREIGN PATENT DOCUMENTS

| EP | 0 600 832 A1 | 11/1993 | ......... C07C/237/30 |
| GB | 1 405 308 | 9/1975 | ......... C07D/213/60 |
| WO | 95/17888 | 7/1995 | ......... A61K/31/165 |
| WO | 97/19065 | 5/1997 | ......... C07D/239/42 |
| WO | 9818782 | * 5/1998 | |
| WO | 98/18782 | 5/1998 | ......... C07D/401/04 |
| WO | WO 98/41512 A1 | 9/1998 | |
| WO | 99/31073 | 6/1999 | ......... C07D/239/48 |

OTHER PUBLICATIONS

"Antifungal Activity of 2,4–Disubstituted Pyrimidine–5–carboxylates", Fabian et al, Indian J. Chem., vol. 16B, Oct. 1978.

International Search Report.

European Search Report dated Aug. 28, 2002.

* cited by examiner

Primary Examiner—Mukund J. Shah
Assistant Examiner—Sudhaker B. Patel
(74) Attorney, Agent, or Firm—Sughrue Mion, PLLC

(57) ABSTRACT

A nitrogen-containing six-membered heterocyclic compound having substituents —X—A—$R^3$, —N($R^1$)-(Ph substituted by $R^2$), and —$CONH_2$, a salt thereof, a prodrug thereof, and a Syk inhibitor containing the same as an active ingredient. (In the formula, A: a (substituted) lower alkylene, a (substituted) arylene, or the like; X: $NR^4$, $CONR^4$, $NR^4CO$, O, or S; $R^1$, $R^4$: H, a lower alkyl, —CO-lower alkyl, or —$SO_2$-lower alkyl; $R^2$: H, a (substituted) lower alkyl, —O-lower alkyl, —S-lower alkyl, —O-aryl, nitro, cyano, or the like; $R^3$: —$CO_2H$, —$CO_2$-lower alkyl, -lower alkylene-$CO_2H$, —$NH_2$, -alkylene-$NH_2$ or the like.

5 Claims, No Drawings

HETEROCYCLECARBOXAMIDE DERIVATIVE

TECHNICAL FIELD

The present invention relates to a heterocyclecarboxamide derivative useful as a medicament, particularly a Syk inhibitor.

BACKGROUND OF THE INVENTION

It is known that type I (immediate type) allergic reaction which plays a main role at allergic diseases as typified by bronchial asthma, allergic rhinitis or atopic dermatitis is initiated by the interaction between an extrinsic antigen such as pollen or house dust and immunoglobulin E (IgE) specific thereto. IgE is captured on the cell surface of mast cell and basophile manifesting IgE receptor (Fc ε RI) having a high affinity. When the antigen binds thereto and cross-links the receptor, the cell is activated and inflammatory mediators such as histamine, serotonin and the like inducing anaphylaxis reaction are released from cytoplasmic secretory granules. Also, it is known that the production of cytokine which takes part in the progress of inflammatory reactions is accelerated.

It is known that at least two types of cytoplasmic tyrosine kinase, i.e., Lyn (Eiseman, E. and Bolen, J. B., Nature, 355: 78–80 (1992)) and Spleen tyrosine kinase (Syk) (Taniguchi, T. et al., J. Biol. Chem., 266: 15790–15796 (1991)), are concerned in the intracellular signal transduction which accompanies this Fc ε RI activation. It is known that Syk undergoes tyrosine phosphorylation by the action of Lyn after crosslinking of Fc ε RI by an antigen, whereby the activity of the tyrosine kinase increases (Hutchcroft, J. E. et al., Proc. Natl. Acad. Sci. USA, 89: 9107–9111 (1992)). It has been also shown that the activation of Syk are necessary for the degranulation and cytokine production acceleration induced by the activation of Fc ε RI (Rivera, V. M. and Brugge, J. S., Mol. Cell. Biol., 15: 1582–1590 (1995)).

Moreover, it is known that Syk is essential for a life-extending signal of eosinophiles mediated by GM-CSF receptor, because antisense oligonucleotide of Syk inhibits the eosinophile's life-extending action of GM-CSF (Yousefi, S. et al., J. Exp. Med., 183: 1407–1414 (1996)).

As described above, it is expected that Syk takes part in allergic or inflammatory reaction through controlling the functions of mast cell, basophile, and eosinophile.

In addition, Syk is suggested to be concerned in various diseases as described below.

It has been reported that Syk is deeply concerned in the phosphatidylinositol metabolism and increase in the intracellular calcium concentration caused by the stimulation of B cell antigen receptor and thus plays an important role at the activation of B cells (Hutchcroft, J. E. et al., J. Biol. Chem., 267: 8613–8619 (1992) and Takata, M. et al., EMBO J., 13: 1341–1349 (1994)). In consequence, a Syk inhibitor may control the function of B cell and therefore is expected as an therapeutic agent for the diseases in which the antibody produced by B cell are concerned.

Also, it has been reported that Syk associates with a T cell antigen receptor and quickly undergoes tyrosine phosphorylation and is activated through crosslinking of the receptor. Accordingly, there is shown a possibility that Syk synergistically acts in combination with a tyrosine kinase such as Lck, ZAP-70, or the like to take part in the T cell activation signal (Couture, C. et al., Proc. Natl. Acad. Sci. USA, 91: 5301–5305 (1994) and Couture, C. et al., Mol. Cell. Biol., 14: 5249–5258 (1994)).

Moreover, it has been reported that the tyrosine phosphorylation of intracellular protein and the phagocytosis induced by stimulation of immunoglobulin G (IgG) receptor (Fc γ R) are considerably inhibited in macrophages derived from Syk deficient mouse (Crowley, M. T. et al., J. Exp. Med., 186: 1027–1039 (1997)). Therefore, Syk plays an extremely important role in the Fc γ R-mediated phagocytosis of macrophage, and it is shown that Syk is concerned in tissue damage induced by antibody-dependent cellular cytotoxicity (ADCC).

Furthermore, it has been reported that the release of arachidonic acid and serotonin and the aggregation of platelets induced by collagen are markedly inhibited in platelets derived from Syk deficient mouse (Poole, A. et al., EMBO J., 16: 2333–2341 (1997)), so that participation in anticoagulation is also shown.

And, as compounds having a Syk inhibitory action, there have been reported a 2-anilinopyrimidine derivative (WO98/18782) represented by the following formula:

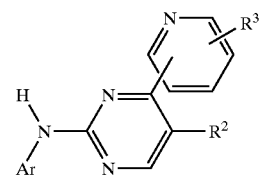

(wherein Ar represents an aromatic cyclic group which may be substituted, and $R^2$ represents H, a halogen, or a group represented by $-X^1-R^{2a}$. Refer to the publication for other symbols), and a natural product derived from a plant, Piceatannol (Oliver, J. M. et al., J. Biol. Chem., 269: 29697–29703 (1994)).

Moreover, as heterocyclecarboxamide derivatives having a substituted amino group, the following compound is disclosed in Indian J. Chem., Sect. B, 16B(10), 932–933 (1978),

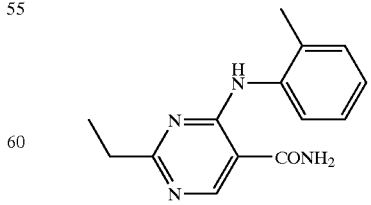

the following compound in EP475206 and U.S. Pat. No. 5,104,877,

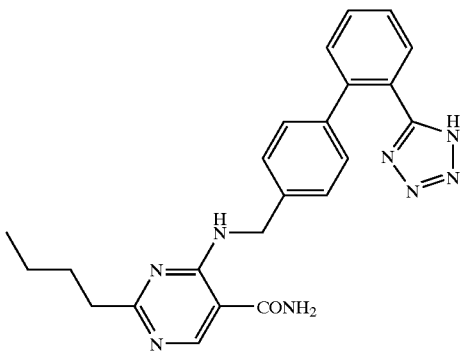

and the following compound in Japanese Patent Laid-Open No. 94677/1974,

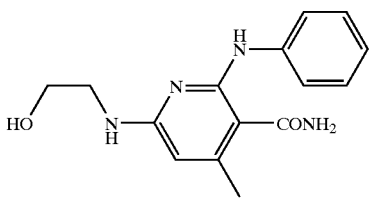

but the action on Syk of these compounds is neither disclosed nor suggested.

DISCLOSURE OF THE INVENTION

As a result of the extensive studies on the compounds inhibiting Syk, the present inventors have found that a heterocyclecarboxamide derivative has a satisfactory Syk inhibitory activity and is useful as an agent for preventing, treating, or diagnosing diseases in which Syk takes part, and thereby have accomplished the invention.

Namely, the invention relates to a novel heterocyclecarboxamide derivative represented by the following general formula (I) or a pharmaceutically acceptable salt thereof, and a medicament comprising the same as the active ingredient.

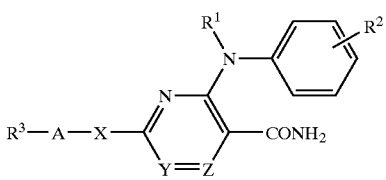

(I)

(wherein the symbols in the formula have the following meanings.

A: a lower alkylene which may have substituent(s), an arylene which may have substituent(s), a heteroarylene which may have substituent(s), a cycloalkylene which may have substituent(s), or H;

X: $NR^4$, $CONR^4$, $NR^4CO$, O, or S;

a dotted line between Y and Z: presence (Y=Z) or absence (Y—Z) of a bond;

Y—Z: $N(R^5)$—C(O), C(O)—$N(R^5)$, $N(R^5)$—$N(R^5)$, or C(O)—C(O);

Y=Z: $N=C(R^6)$, $C(R^7)=N$, N=N, or $C(R^7)=C(R^7)$;

$R^1$, $R^4$: H, a lower alkyl, —CO-lower alkyl, or —$SO_2$-lower alkyl;

$R^2$: H, a lower alkyl, a halogen, a lower alkyl substituted by halogen(s), —O-lower alkyl, —S-lower alkyl, —O-aryl,
—O-lower alkylene-aryl, —S-lower alkylene-aryl, nitro, cyano, —$OCH_2O$—, or —(CH=CH-CH=CH)—;

$R^3$: —$CO_2H$, —$CO_2$-lower alkyl, -lower alkylene-$CO_2H$, -lower alkylene-$CO_2$-lower alkyl, —CONHOH, —CONHO-lower alkyl, -lower alkylene-CONHOH, -lower alkylene-CONHO-lower alkyl, —$NH_2$, —($NH_2$ in a prodrug form), -lower alkylene-$NH_2$, or -lower alkylene-($NH_2$ in a prodrug form);

$R^5$: H or a lower alkyl group;

$R^6$: a lower alkyl, —OH, —O-lower alkyl, —O-aryl which may have substituent(s), —O-lower alkylene-aryl which may have substituent(s), —$NR^1$-aryl which may have substituent(s), —CO-lower alkyl, or -aryl group which may have substituent(s);

$R^7$: the same or different, H or the same group as $R^6$. The same shall apply to the following).

By the way, when Y=Z represents $N=C(R^6)$, $C(R^7)=N$, N=N, or $C(R^7)=C(R^7)$ in the formula, the central heterocycle part:

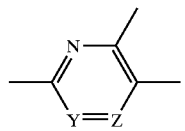

represents any of the following formulae:

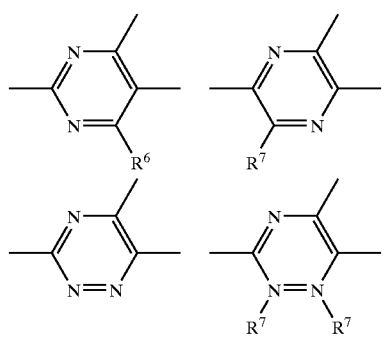

and when Y—Z represents $N(R^5)$—C(O), C(O)—$N(R^5)$, $N(R^5)$—$N(R^5)$, or C(O)—C(O) in the formula, the central heterocycle part represents any of the following formulae.

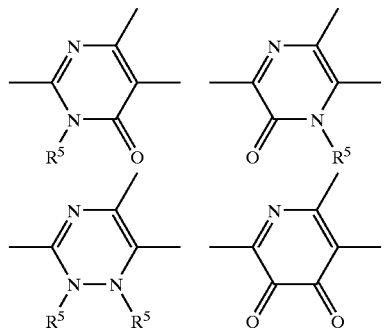

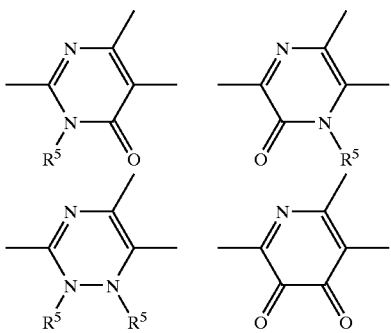

In the above formulae, there is a case that tautomers are present as the case of the compound wherein $R^6$ of N=C($R^6$) is OH and the compound wherein $R^5$ of C($R^5$)—C(O) is H or the case of the compound wherein $R^7$ of C($R^7$)=N is OH and the compound wherein $R^5$ of C(O)—N($R^5$) is H. The invention also includes these isomers.

According to the invention, also provided is a pharmaceutical composition, particularly a Syk tyrosine kinase inhibitor comprising the above heterocyclecarboxamide derivative or a salt thereof.

The following will explain the invention in detail.

In this specification, the term "lower" means a linear or branched hydrocarbon chain having from 1 to 6 carbon atoms. The "lower alkyl group" is preferably a lower alkyl group having from 1 to 4 carbon atoms, and more preferred is methyl, ethyl, or isopropyl group. The "lower alkylene" is preferably a lower alkylene having from 1 to 4 carbon atoms, and particularly preferred is methylene, ethylene, or butylene.

The "halogen" includes F, Cl, Br, and I. The "lower alkyl substituted by halogen(s)" is preferably fluoromethyl, trifluoromethyl, or trifluoroethyl group.

The "arylene", "heteroarylene", and "cycloalkylene" mean divalent groups formed by removing hydrogen atom at any position of "aryl group", "heteroaryl group", and "cycloalkyl group", respectively.

The "aryl group" is preferably a monocyclic to tricyclic aryl group having from 6 to 14 carbon atoms, more preferably, a phenyl group or a naphthyl group. Also, the phenyl group may be condensed with a five- to eight-membered cycloalkyl ring to form, for example, an indanyl group or a 5,6,7,8-tetrahydronaphthyl group, which combines from the aromatic ring. The "arylene" is preferably 1,2-phenylene or 1,4-phenylene.

The "cycloalkyl group" is preferably a cycloalkyl group having from 3 to 8 carbon atoms. More preferred as the "cycloalkylene" is cyclohexane-1,1-diyl, 1,2-cyclopentylene, 1,2-cyclohexylene, or 1,4-cyclohexylene. Also, the cycloalkyl group may be condensed with a benzene ring to form, for example, 1- or 2-indanyl or a 1,2,3,4-tetrahydronaphthyl group.

The "heteroaryl group" is a five- to six-membered monocyclic heteroaryl group having from 1 to 4 hetero atoms selected from O, S and N, and is preferably pyridyl, pyrimidinyl, imidazolyl, thienyl, furyl, or thiazolyl group.

Substituents of the "lower alkylene which may have substituent(s)", "arylene which may have substituent(s)", "heteroarylene which may have substituent(s)", "cycloalkylene which may have substituent(s)" and "aryl which may have substituent(s)" are not particularly limited so long as they can be used as substituents of these rings, but are preferably the substituents selected from the following group. One to four of these substituents may be present.

-lower alkyl, -halogen, -lower alkyl substituted by halogen(s), -cycloalkyl, -heteroaryl, -nitrogen-containing saturated heterocycle, -vinyl, -(1-propenyl), -ethynyl, —OH, —O-lower alkyl, —O-lower alkylene-aryl, —O-aryl, —O-lower alkylene-aryl-O-lower alkyl, —S-lower alkylene-aryl, —S-lower alkylene-aryl-O-lower alkyl, —CONHOH, —CONH-lower alkyl, —CON(lower alkyl)$_2$, —NO$_2$, and —CN.

Moreover, the "—NH$_2$ in a prodrug form" means any of the groups well known by those skilled in the art, which forms —NH$_2$ under physiological conditions. For example, there are mentioned the groups described in Prog. Med., 5, 2157–2161 (1985) and "Iyakuhin no Kaihatsu (Pharmaceutical Research and Development)" (Hirokawa Publishing Co., 1990), vol. 7, Bunshi Sekkei (Drug Design) 163–198. Preferred are (Z)-3-[2-(acetoxy)phenyl]-2-propenoylamino-, (acetoxy)methoxycarbonylamino-, 4-azidobenzyloxycarbonylamino-, (5-methyl-2-oxo-1,3-dioxol-4-en-4-yl)methoxycarbonylamino- and [(2-hydroxyphenyl)(phenyl)methylidene]amino-, and other groups of this type known by those skilled in the art are also included. In addition, prodrugs with regard to the groups such as OH and COOH are also included in the invention.

The substituent $R^2$ on the anilino group in the formula (I) represents one group or a plural number of groups (e.g., "3, 5-Me" means "3,5-dimethyl"). $R^2$ also represents —OCH$_2$O— or —(CH=CH-CH=CH)—, wherein —OCH$_2$O means a methylenedioxy group and —(CH=CH-CH=CH)—, wherein —OCH$_2$O— means a methylenedioxy group and —(CH=CH-CH=CH)— means a naphthyl group together with the adjacent benzene ring.

Among the compounds of the invention, A in the formula (I) is preferably a lower alkylene or cycloalkylene, more preferably ethylene or cyclohexylene. $R^3$ is preferably —CO$_2$H, —CO$_2$-lower alkyl, -lower alkylene-CO$_2$H, -lower alylene-CO$_2$-lower alkyl, —NH$_2$, —(NH$_2$ in a prodrug form), -lower alkylene-NH$_2$, or -lower alkylene-(NH$_2$ in a prodrug form), further preferably —NH$_2$, —(NH$_2$ in a prodrug form), -lower alkylene-NH$_2$, or -lower alkylene-(NH$_2$ in a prodrug form), more preferably —NH$_2$ or —(NH$_2$ in a prodrug form). X is preferably NR$_4$. Y—Z and Y=Z are preferably N($R^5$)—C(O), C(O)—N($R^5$), N=C($R^6$), C($R^7$)=N, or C($R^7$)=C($R^7$), further preferably N=C($R^6$), C($R^7$)=N, or C($R^7$)=C($R^7$).

Among the compounds of the present invention, the following compounds can be mentioned as most preferred compounds: 6-(2-aminoethylamino)-2-(3-ethylanilino)pyridine-3-carboxamide, 6-(2-aminoethylamino)-2-(3-trifluoromethylanilino)pyridine-3-carboxamide, 2-(2-aminoethylamino)-4-hydroxy-6-(3-methylanilino)pyrimidine-5-carboxamide, 6-(cis-2-aminocyclohexylamino)-2-(3-methylanilino)pyridine-3-carboxamide, 6-(cis-2-aminocyclohexylamino)-2-(3,5-dimethylanilino)pyridine-3-carboxamide, 5-(cis-2-aminocyclohexylamino)-3-(3-methylanilino)pyrazine-2-carboxamide, 5-(cis-2-aminocyclohexylamino)-3-(3-methoxyanilino)pyrazine-2-carboxamide, 5-(cis-2-aminocyclohexylamino)-3-(3-phenoxyanilino)pyrazine-2-carboxamide, 5-(cis-2-aminocyclohexylamino)-3-(4-methylsulfanylanilino)pyrazine-2-carboxamide, 5-(cis-2-aminocyclohexylamino)-3-(3,5-dimethoxyanilino)pyrazine-2-carboxamide, 2-(cis-2-aminocyclohexylamino)-4-hydroxy-6-(3-methylanilino)pyrimidine-5-carboxamide, 2-(cis-2-aminocyclohexylamino)-4-(3-bromoanilino)-6-hydroxypyrimidine-5-carboxamide, 2-(cis-2-aminocyclohexylamino)-4-(2-chlorophenoxy)-6-(3-methylanilino)pyrimidine-5-carboxamide.

Depending on the kinds of substituents, the compound of the invention may exist in the form of geometrical isomers or tautomers, and isolated forms or mixtures of these isomers are included in the invention. Also, the compound of the present invention may contain an asymmetric carbon atom in some cases, so that isomers based on the asymmetric carbon atom may exist. Mixtures or isolated forms of these optical isomers are included in the present invention.

Also, the compound of the present invention sometimes forms an acid addition salt or, depending on the kinds of substituents, a salt with a base. Such salts are pharmaceutically acceptable salts, and illustrative examples thereof include acid addition salts with inorganic acids such as hydrochloric acid, hydrobromic acid, hydroiodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like; salts with inorganic bases such as sodium, potassium, magnesium, calcium, aluminum and the like or with organic bases such as methylamine, ethylamine, ethanolamine, lysine, ornithine and the like; ammonium salts, and the like. In addition, various types of hydrates and solvates and polymorphic substances of the compound (I) of the invention and salts thereof are also included in the invention.

(Production Methods)

The compound of the present invention and pharmaceutically acceptable salt thereof can be produced by applying various known synthesis methods, making use of their characteristics based on the basic structures or kinds of substituents. At that time, depending on the kinds of functional groups, it is sometimes effective, from the viewpoint of the production techniques, to replace said functional group by an appropriate protecting group, namely a group which can be easily converted into said functional group, at the step of the starting material or intermediate. Thereafter, the desired compound can be obtained by removing the protecting group as occasion demands. Examples of such functional groups include amino group, hydroxyl group, carboxyl group and the like. Examples of their protecting groups include the protecting groups described in "Protective Groups in Organic Synthesis (2nd. Ed.)" edited by Greene and Wuts, and these groups are optionally used depending on the reaction conditions.

The following describes typical production methods of the compounds of the invention.

First Production Method

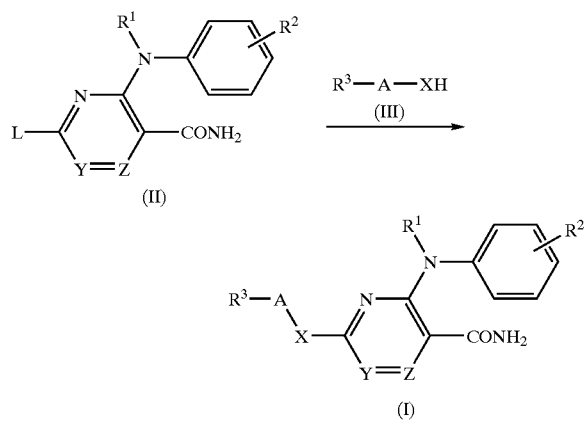

(wherein L represents a leaving group. Other symbols have the same meanings as described above)

This production method is a method in which the compound of the present invention represented by the general formula (I) is obtained by reacting a compound (II) with a compound (III). In the method, examples of the leaving group L include halogen atoms and methylsulfanyl, 1H-benzotriazol-1-yloxy, methylsulfinyl, methanesulfonyl, methanesulfonyloxy, p-toluenesulfonyloxy, trifluoromethanesulfonyloxy, and the like.

The reaction can be carried out from under cooling to under heating to reflux using the compounds (II) and (III) in equimolar amounts or in an excess amount of one of them, without solvent or in a solvent inert to the reaction such as aromatic hydrocarbons, e.g., benzene, toluene, xylene and the like; ethers, e.g., diethyl ether, tetrahydrofuran (THF), dioxane and the like; halogenated hydrocarbons, e.g., dichloromethane, 1,2-dichloroethane, chloroform and the like; N,N-dimethylformamide (DMF); N,N-dimethylacetamide (DMA); N-methylpyrrolidone; ethyl acetate; acetonitrile; and the like. The reaction temperature can be optionally selected depending on the compounds. Depending on the compounds, it is advantageous in some cases to carry out the reaction in the presence of an organic base (preferably diisopropylethylamine, N-methylmorpholine, pyridine, or 4-(N,N-dimethylamino) pyridine) or a metal salt base (preferably sodium hydride, potassium carbonate, sodium carbonate, sodium hydrogen carbonate, sodium hydroxide, or potassium hydroxide).

Second Production Method

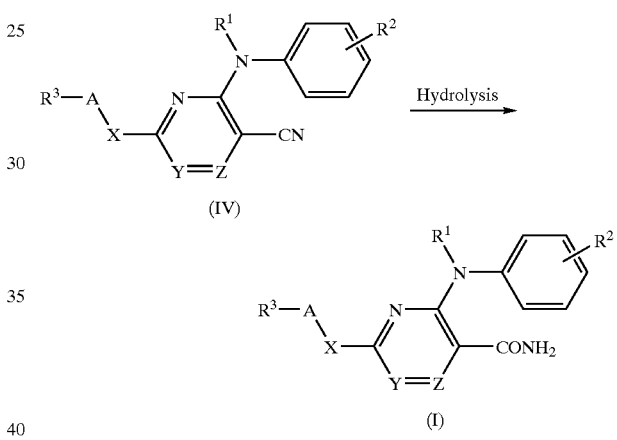

(wherein the symbols in the scheme are as defined in the above)

This production method is a method in which the compound (I) of the invention is obtained by converting the nitrile group of a nitrile compound (IV) into a carboxamido group under various conditions. The reaction can be carried out from at room temperature to under heating to reflux without solvent or in a solvent inert to the reaction such as aromatic hydrocarbons; ethers; halogenated hydrocarbons; alcohols, e.g., methanol, ethanol and the like; DMF; pyridine; water; dimethyl sulfoxide (DMSO); and the like, in the presence of a mineral acid, e.g., sulfuric acid, hydrochloric acid, hydrobromic acid or the like; an organic acid, e.g., formic acid, acetic acid or the like; or a base, e.g., sodium hydroxide, potassium hydroxide, potassium carbonate, sodium carbonate, ammonia or the like. It is advantageous in some cases to carry out the reaction in the presence of hydrogen peroxide or the like, for the purpose of effecting smooth progress of the reaction. The reaction temperature can be selected optionally, depending on the compound.

Production Method of Starting Compounds

Starting compounds (II) and (IV) for the compound of the invention can be produced in the usual way, for example, by applying known reactions shown in the following scheme of synthetic pathway.

Production Method 1

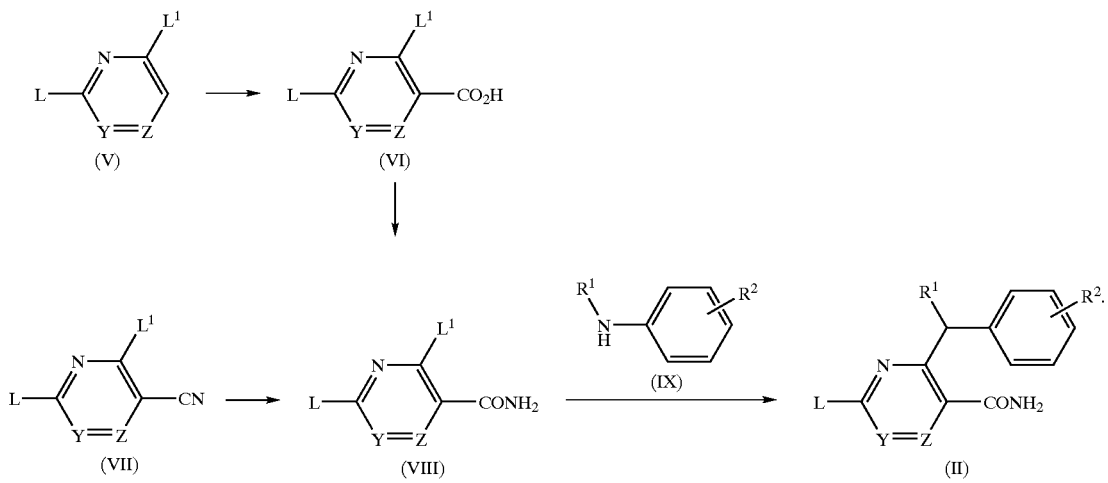

(wherein $L^1$ represents a leaving group similar to the above L. Other symbols are as defined in the above)

A starting compound (II) can be produced by substitution reaction between a compound (VIII) and an aniline derivative (IX). The reaction can be carried out under conditions similar to the above first production method.

The intermediate (VIII) can be produced by treating a carboxylic acid compound (VI) with ammonia in the presence of a condensing agent (e.g., dicyclohexylcarbodiimide (DCC), diisopropylcarbodiimide (DIPC), 1-ethyl-3-(3-dimethylaminopropyl)carbodiimide (WSC), 1,1'-carbonylbis-1H-imidazole (CDI), or the like) and, in some cases, an additive (e.g., N-hydroxysuccinimide (HONSu), 1-hydroxybenzotriazole (HOBt), or the like) Examples of the solvent include aromatic hydrocarbons, ethers, halogenated hydrocarbons, DMF, pyridine, and the like. These solvents may be used solely or as a mixture of two or more of them.

The intermediate (VI) can be produced by introducing a carboxylic acid into a compound (V) under various conditions. The reaction can be carried out from at −78° C. to under ice cooling in a solvent inert to the reaction such as ethers or hexane by converting the compound into an anion under a basic condition (e.g., n-butyllithium, sec-butyllithium, tert-butyllithium, 2,2,6,6-tetramethylpiperidine lithium salt (LiTMP), diisopropylamine lithium salt (LDA), or the like, or N,N,N',N'-tetramethylethylenediamine, hexamethylphosphoramide (HMPA), DMA, or the like may be added thereto in order to assist the reaction), and then adding dry ice or blowing carbon dioxide into the solution. The reaction temperature can be selected optionally, depending on the compound.

Moreover, the intermediate (VIII) can be also produced by hydrolyzing a nitrile compound (VII). The conditions similar to those in the above second production method can be adopted as the reaction conditions.

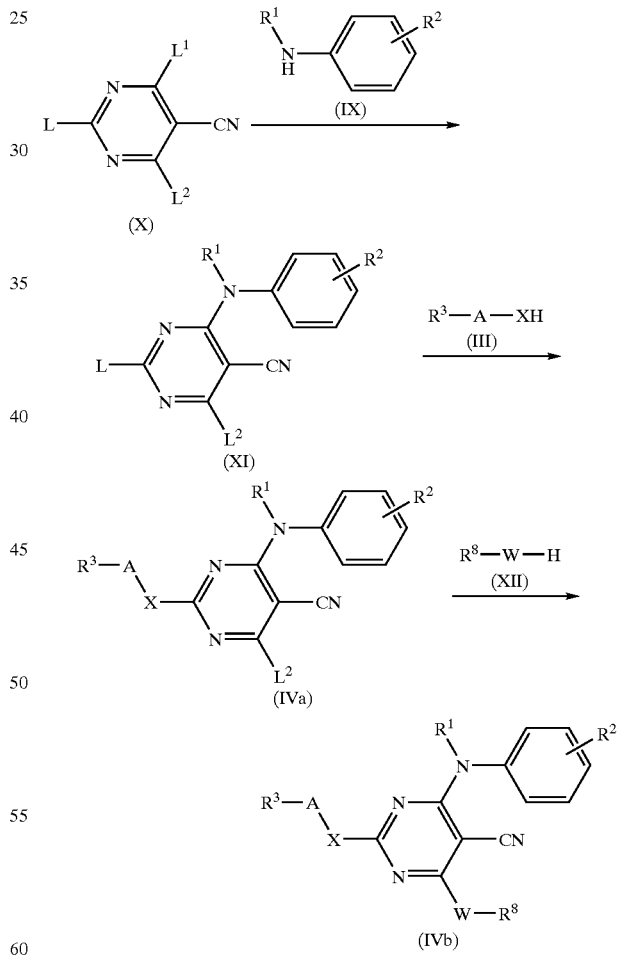

(wherein $L^2$ represents a leaving group similar to the above L or $R^6$ or $R^7$, $R^8$ represents -aryl which may have substituent(s), -lower alkylene-aryl which may have subostituent(s), or -aryl group which may have substituent (s), and W represents O or $NR^1$. Other symbols are defined as in the above)

The starting compound (IVb) can be produced by reacting a compound (IVa) with a compound (XII). The reaction can be carried out from under cooling to under heating in a solvent inert to the reaction such as aromatic hydrocarbons, ethers, halogenated hydrocarbons, DMF, DMSO, pyridine, or the like. It is advantageous in some cases to carry out the reaction in the presence of a metal salt base, for the purpose of effecting smooth progress of the reaction.

The starting compound (IVa) can be produced by reacting a compound (XI) with the compound (III). The conditions similar to those in the above first production method can be adopted.

The intermediate (XI) can be produced by the substitution reaction between a nitrile compound (X) and an aniline compound (IX). The conditions similar to those in the above first production method can be adopted.

Furthermore, the compound wherein the substituent $R^1$ is an alkyl, —CO-lower alkyl, or —$SO_2$-lower alkyl can be produced in the usual way using the compound wherein $R^1$ is H. The introduction of an alkyl group can be carried out using an alkyl halide or an alkyl ester in a similar manner to the above first production method. The introduction of the —CO-lower alkyl or —$SO_2$-lower alkyl group can be carried out from under cooling to under heating in a solvent inert to the reaction such as halogenated hydrocarbons, ethers, DMF, or the like by an acid halide method, a mixed or symmetric acid anhydride method, an active ester method, a condensing agent (DCC, WSC, CDI, etc.) method, or the like. It is advantageous in some cases to carry out the reaction in the presence of a base, for the purpose of effecting smooth progress of the reaction.

The reaction product obtained by each of the aforementioned production methods is isolated and purified as a free compound, a salt thereof or any of various types of solvate such as hydrate. Salts can be produced by the usual salt-forming treatment.

The isolation and purification are carried out by employing usual chemical operations such as extraction, concentration, evaporation, crystallization, filtration, recrystallization, various chromatographic techniques, and the like.

Various isomers can be isolated in the usual way making use of a physicochemical difference among the isomers. For example, optical isomers can be separated by a general optical resolution method such as fractional crystallization or a chromatography. In addition, an optical isomer can also be produced from an appropriate optically active starting compound.

INDUSTRIAL APPLICABILITY

The compound of the invention is useful as an active ingredient for pharmaceutical preparations. Particularly, since it has a Syk inhibitory activity, it is useful as an agent for preventing and treating the following diseases in which Syk takes part. The diseases in which an allergic or inflammatory reaction becomes the main cause (e.g., asthma, rhinitis, atopic dermatitis, contact dermatitis, nettle rash, food allergy, conjunctivitis, vernal conjunctivitis and the like); autoimmune diseases (e.g., rheumatoid arthritis, systemic lupus erythematosus, psoriasis and the like); cancers and the like; diseases in which immune reaction takes part (e.g., rejection at the time of organ transplantation, graft versus host disease and the like); diseases in which ADCC takes part (e.g., autoimmune hemolytic anemia, myasthenia gravis and the like); and diseases in which platelet agglutination takes part.

Actions of the compound of the invention have been confirmed by the following pharmacological tests.
1. Syk Tyrosine Kinase Inhibition Test
1) Preparation of Syk Protein Human Syk gene, in the form where a gene of FLAG tag consisting of 8 amino acid residues was linked to the 3'-end, was cloned using RT-PCR method from total RNA prepared from Jurkat cells. The amplified cDNA was incorporated into a vector, pFASTBAC HT, contained in Baculovirus Expression System (GIBCO BRL Inc.). The pFASTBAC HT is designed in such a manner that a His tag consisting of 6 histidine residues can be fused to the 5'-end of Syk. This plasmid DNA was introduced into competent cells, DH10BAC, contained in the Baculovirus Expression System to prepare DNA of recombinant virus. Thereafter, the recombinant virus (culture supernatant) was obtained by transfection of the DNA of recombinant virus into Sf-9 cells (ATCC).

The Sf-9 cells infected with this recombinant virus were recovered and lysed using a lysis buffer containing 1% Triton X-100. After centrifugation of the soluble fraction, the supernatant was mixed with TALON resin (CLONTECH) to allow the His-tag fused protein of Syk to be adsorbed by the resin. After several times of washing of the resin, the His-tag fused protein of Syk was eluted with a buffer containing imidazole.
2) Preparation of Band 3 Peptide A peptide of 18 amino acid residues (MEELQDDYEDMMEENLEQ) (SEQ ID NO:1) containing Tyr-8 of human erythrocyte Band 3 (Harrison, M. L. et al., J. Biol. Chem., 269: 955–959 (1994)) was synthesized using a peptide synthesizer. Using a biotinylation kit manufactured by Pierce, the N-terminal of the peptide in a resin-linked state was biotinylated, and purification was carried out using an HPLC.
3) Measurement of Syk Tyrosine Kinase Activity Using an SPA System SPA (Scintillation Proximity Assay) is a system developed by Amersham making use of a phenomenon in which scintillation occurs when a molecule having a radioactivity is in the proximity of (linked to) the surface of plastic beads containing a scintillant included therein. These beads are coated in advance with streptoavidin to which the biotin moiety of substrate peptide is bound.

A 2 $\mu$l portion of a DMSO solution of a compound to be tested (final DMSO concentration, 4%) per well was added to 50 $\mu$l of a reaction solution (composition: 0.2 $\mu$g Syk, 50 mM Tris-HCl (pH 8), 10 mM $MgCl_2$, 50 mM NaCl, 1 mM DTT, 0.4 $\mu$M Band 3 peptide and 0.1 $\mu$Ci [$\gamma$-$^{33}$P]ATP (10 mCi/ml, Amersham)). This was prepared in OptiPlate™ (PACKARD) and allowed to stand at room temperature (20 to 25° C.) for 1 hour to effect tyrosine phosphorylation.

The reaction was terminated by adding PBS containing 0.25 mg SPA beads, 50 $\mu$M ATP, 5 mM EDTA and 1% Triton X-100 (reaction-terminating solution) in an amount of 150 $\mu$l per well.

The plate was sealed, stirred, allowed to stand at room temperature for 15 minutes and then centrifuged at 1,500 rpm for 3 minutes to precipitate the SPA beads. Radioactivity of each well was measured using TOP COUNT (PACKARD), and the tyrosine phosphorylation activity by Syk was calculated.
4) Results The compounds of Examples of the invention exhibited an inhibitory activity of 0.05 $\mu$M or less as $IC_{50}$ value against Syk. However, comparative compounds having a substituent in the carboxamido group, 2-(2-aminoethylamino)-N- methyl-4-(3-trifluoromethylanilino)pyrimidine-5-carboxamide and 2-(2-aminoethylamino)-N,N-dimethyl-4-(3-trifluoromethylanilino)pyrimidine-5-carboxamide did not exhibit any inhibitory activity at 1 $\mu$M.

2. Serotonin Release Test

This was carried out in accordance with the method reported by Collado-Escobar et al. (Collado-Escobar, D et al. J. Immunol., 144: 3449–3457 (1990)).

The compound of Examples 1, 2, 8, 10, and 11 exhibited an inhibitory activity of 0.1 $\mu$M or less as $IC_{50}$ value against the release of serotonin.

3. Mouse Passive Cutaneous Anaphylaxis (PCA) Test

Male ICR (CD-1) mice of 5 weeks age were sensitized by subcutaneously injecting 10 $\mu$l of anti-dinitrophenyl-IgE (DNP-IgE) (1,000 times dilution of a roughly purified product of ascites of Balb/c mouse to which a DNP-IgE producing hybridoma had been administered by intraperitoneal injection) into the right ear pinna while lightly anesthetizing with ether. After 24 hours of the sensitization, 200 $\mu$l of 0.5% Evans blue solution containing 50 $\mu$g of DNP-conjugated bovine serum albumin was intravenously administered, and, after 30 minutes, each mouse was sacrificed through exsanguination to isolate both ears. Each test compound or the vehicle alone as a control was administered subcutaneously 30 minutes before the antigen challenge or orally 2 hours before the challenge. The dye in the tissues was extracted with formaride and colorimetrically determined at 620 nm. A value obtained by subtracting the dye content of the left ear from the dye content of the right ear was used as the amount of dye leaked into the tissues by the PCA reaction.

The PCA inhibition ratio by the test compound was calculated based on the following equation. In the formula, C: amount of the dye leaked into the tissue at the time of the administration of the vehicle alone, and x: amount of the dye leaked into the tissue at the time of the administration of the test compound.

Inhibition ratio (%)=$\{C-X\}\times 100/C$

The compounds of Examples 1, 2, 8, 10 and 11 excellently suppressed PCA reaction.

From the results of the above experiments 1 to 3, it is confirmed that the compound of the invention inhibits the release of inflammatory mediator and suppresses the anaphylaxis reaction, and especially has a Syk inhibitory activity. Thus, it is obvious that the compound is useful as an agent for preventing and treating the diseases in which Syk takes part.

The pharmaceutical composition comprising one or two or more of the compounds represented by the general formula (I) or salts thereof as the active ingredient can be prepared by generally used methods using pharmaceutical carriers, fillers and the like which are generally used in this field. Its administration form may be either oral administration by tablets, pills, capsules, granules, powders, liquids and the like, or parenteral administration by intravenous, intramuscular and the like injections, suppositories, eye drops, eye ointments, percutaneous liquids, ointments, percutaneous adhesive preparations, transmucosal liquids, transmucosal adhesive preparations, inhalants and the like.

The solid composition for use in the oral administration according to the invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone, magnesium aluminate metasilicate. In accordance with a conventional method, the composition may contain other additives than the inert diluent, such as a lubricant, e.g., magnesium stearate or the like, a disintegrating agent, e.g., calcium cellulose glycolate or the like, a stabilizing agent, e.g., lactose or the like, and a solubilization-assisting agent, e.g., glutamic acid, aspartic acid or the like. If necessary, tablets or pills may be coated with a sugar or a film of gastric or enteric substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol. In addition to the inert diluent, this composition may also contain auxiliary agents such as a solubilizing agent, a moistening agent, a suspending agent and the like, as well as sweeteners, flavors, aromatics and antiseptics.

The injections for parenteral administration include aseptic aqueous or non-aqueous solutions, suspensions and emulsions. The aqueous solutions and suspensions include distilled water for injection or physiological saline. For the non-aqueous solutions and suspensions, propylene glycol, polyethylene glycol, vegetable oil such as olive oil, alcohols such as ethanol, polysorbate 80 (trade name) and the like may be used. Such a composition may further contain auxiliary agents such as a tonicity, an antiseptic, a moisturizing agent, an emulsifying agent, a dispersing agent, a stabilizing agent (e.g., lactose) and a solubilization-assisting agent (e.g., glutamic acid or aspartic acid). These compositions are sterilized by filtration through a bacteria-retaining filter, blending of a germicide, or irradiation. Alternatively, they may be used by firstly making into sterile solid compositions and dissolving them in sterile water or a sterile solvent for injection prior to their use.

The transmucosal preparations such as transnasal preparations are in the solid, liquid or semisolid form and can be produced by methods known per se. For example, they are formed into a solid, liquid or semisolid state by optionally adding known pH adjusting agents, antiseptics, thickeners, excipients and the like. The transnasal preparations are administered using generally used sprayers, nasal drops containers, tubes, nasal cavity-inserting tools and the like.

In the case of oral administration, the suitable daily dose is generally from about 0.001 to 100 mg/kg body weight, preferably from 0.1 to 10 mg/kg, which is administered in one portion or by dividing into two to four doses. In the case of intravenous injection, the suitable daily dose is from about 0.0001 to 10 mg/kg body weight, which is administered in one portion or by dividing into several doses. In the case of transmucosal preparations, a dose of from about 0.001 to 10 mg/kg body weight is administered once a day or by dividing into several doses. The dose is optionally determined in consideration of symptoms, age, sex and the like at individual case.

BEST MODE FOR CARRYING OUT THE INVENTION

The following describes the invention further in detail based on Examples. Compounds of the invention are not limited to the compounds described in the following Examples. In addition, methods for producing starting compounds are shown as Reference Examples.

Reference Example 1

To a THF solution of 2,2,6,6-tetramethylpiperidine was added n-butyllithium under ice cooling and was further added a THF solution of 2,6-dichloropyrazine at −78° C. After 30 minutes of stirring, dry ice was added to the reaction mixture and, after 30 minutes of stirring, 1 M hydrochloric acid was added thereto. Thereafter, purification in the usual way afforded 3,5-dichloropyrazine-2-carboxylic acid (pale yellow solid). FAB-MS: 191 (M−H)⁻.

Reference Example 2

Thionyl chloride was added to 3,5-dichloropyrazine-2-carboxylic acid, followed by heating to reflux for 30 minutes. Then, solvent was removed by evaporation under reduced pressure. Dichloromethane was added to the residue and aqueous ammonia was added thereto under ice cooling. After 1 hour of stirring, purification in the usual way afforded 3,5-dichloropyrazine-2-carboxamide (pale yellow solid). FAB-MS: 192 (M+H)⁺.

Reference Example 3

Conc. hydrochloric acid was added to (1'S,1R,2S)-N-[2-(1'-phenylethylamino)cyclohexylamino]benzamide monohydrochloride synthesized according to the method described in a literature (W. H. Schlichter and A. W. Frahm, Arch. Pharm., 326, 429–436 (1993)), followed by heating to reflux for 3 days. Thereafter, purification was carried out in the usual way and then formation of a salt was carried out to obtain (1'S,1R,2S)-2-(1'-phenylethylamino)cyclohexylamine dihydrochloride (colorless solid). FAB-MS: 219 (M+H)⁺.

Reference Example 4

To an acetonitrile solution of 3,5-dichloropyrazine-2-carboxamide were added 3-methylaniline and N,N-diisopropylethylamine, followed by heating to reflux for 17 hours. Thereafter, purification in the usual way afforded 5-chloro-3-(3-methylanilino)pyrazine-2-carboxamide (yellow solid).

Reference Example 5

Potassium carbonate and 31% aqueous hydrogen peroxide solution were added to a DMSO solution of 6-(3-bromoanilino)-2-[cis-2-(tert-butoxycarbonylamino)cyclohexylamino]-4-chloropyrimidine-5-carbonitrile, followed by stirring at room temperature for 13 hours. Thereafter, purification in the usual way afforded 6-(3-bromoanilino)-2-[cis-2-(tert-butoxycarbonylamino)cyclohexylamino]-4-hydroxypyrimidine-5-carboxamide (yellow solid).

Reference Example 6 o-Chlorophenol and 60% sodium hydride were added to a mixture of 2-[cis-2-(tert-butoxycarbonylamino)cyclohexylamino]-4-chloro-6-(3-methylanilino)pyrimidine-5-carbonitrile and DMF, followed by stirring at room temperature for 30 minutes and at 70° C. for 5 hours. Thereafter, purification in the usual way afforded 2-[cis-2-(tert-butoxycarbonylamino)cyclohexylamino]-4-(2-chlorophenoxy)-6-(3-methylanilino)pyrimidine-5-carbonitrile (colorless solid).

Reference Example 7

To a mixture of benzyl alcohol and DMF was added 60% sodium hydride under ice cooling and then 2-[cis-2-(tert-butoxycarbonylamino)cyclohexylamino]-6-chloro-4-(3-methylanilino)pyrimidine-5-carbonitrile was added thereto, followed by stirring at 60° C. for 40 minutes. Then, distilled water was added to the reaction liquid and the resulting precipitate was collected by filtration. The filtration product was treated in a similar manner to Reference Example 4 to obtain 2-(cis-2-aminocyclohexylamino)-4-benzyloxy-6-(3-methylanilino)pyrimidine-5-carboxyamide (colorless solid).

In the following, using commercially available compounds or compounds known in literatures and the like, the compounds of Reference Examples 8 to 23 shown in Table 1 were produced in a similar manner to above Reference is Example 4, and the compounds of Reference Examples 24 and 25 shown in Table 1 were produced in a similar manner to Reference Example 5 using corresponding starting materials. Structures and physicochemical data of the compounds of Reference Examples 4 to 25 are shown in Table 1.

EXAMPLE 1

To a mixture of 233 mg of 6-chloro-2-(3-methylanilino)pyridine-3-carboxamide and toluene was added 486 mg of cis-1,2-cyclohexanediamine, followed by heating to reflux for 5 days. The reaction mixture was cooled to room temperature and the resulting precipitate was collected by filtration to obtain 172 mg of 6-(cis-2-aminohexylamino)-2-(3-methylanilino)pyridine-3-carboxamide monohydrochloride as brown solid.

EXAMPLE 2

To a mixture of 605 mg of 5-chloro-3-(3-methylanilino)pyrazine-2-carboxamide and 10 ml of acetonitrile was added 2.76 ml of cis-1,2-cyclohexanediamine, followed by heating to reflux for 4 hours. The reaction mixture was cooled to room temperature and the resulting precipitate was collected by filtration. The resulting solid was dissolved in a mixed solvent of chloroform and 2-propanol. The solution was washed with 1 M aqueous sodium hydroxide solution and saturated saline, successively, and dried over sodium sulfate. Then, the solution was concentrated under reduced pressure and the residue was recrystallized from a mixed solvent of DMF-ethyl acetate to obtain 230 mg of 5-(cis-2-aminohexylamino)-3-(3-methylanilino)pyrazine-2-carboxamide as yellow crystals.

EXAMPLE 3

To a mixture of 558 mg of 2-(cis-2-aminohexylamino)-4-benzyloxy-6-(3-methylanilino)pyrimidine-5-carboxyamide, 10 ml of ethanol, and 20 ml of THF was added 200 mg of 10% palladium-carbon powder, followed by stirring at room temperature for 1 hour under hydrogen atmosphere of normal pressure. Distilled water was added to the reaction mixture, the resulting mixture was filtrated, and the filtrate was concentrated under reduced pressure. The residue was recrystallized from a mixed solvent of ethanol-water to obtain 267 mg of 2-(cis-2-aminohexylamino)-4-hydroxy-6-(3-methylanilino)pyrimidine-5-carboxamide as colorless solid.

EXAMPLE 4

To a mixture of 326 mg of 6-(3-bromoanilino)-2-[cis-2-(tert-butoxycarbonylamino)hexylamino]-4- hydroxypyrimidine-5-carboxamide and 10 ml of methanol was added 5 ml of a solution of 4 M hydrochloric acid-ethyl acetate, followed by stirring at room temperature for 12 hours. After the reaction, the resulting precipitate was collected by filtration to obtain 110 mg of 6-(3-bromoanilino)-2-(cis-2-aminocyclohexylamino)-4-hydroxypyrimidine-5-carboxamide (colorless solid).

The compounds of Examples 5 to 7 shown in Table 2 were produced in a similar manner to Example 1, the compounds of Examples 8 to 11 shown in Table 2 were produced in a similar manner to Example 2, the compounds of Examples 12 to 14 shown in Table 2 were produced in a similar manner to Example 3, and the compounds of Examples 15 and 16 were produced in a similar manner to Example 4, using corresponding raw materials. Structures and physicochemical data of the compounds of Examples 1 to 16 are shown in Table 2.

Also, structures of other compounds of the invention are shown in Tables 3 to 11. These compounds can be easily synthesized according to the aforementioned production methods and the methods described in the Examples, as well as the methods which are obvious to those skilled in the art or modified methods thereof.

The following abbreviations are used in the tables. Also, the number before each substituent group indicates the substitution position, and plural numbers indicates plural substitutions. For example, 3,5-Me indicates 3,5-dimethyl.

Rex: Reference Example number, Ex: Example number, Cmpd: compound number, Ph: phenyl, Me: methyl, Et: ethyl, tBu: tert-butyl, Boc: tBuO-CO-, Bn: benzyl, Ac: acetyl, BCA: cis-2-(tert-butoxycarbonylamino)cyclohexylamino, PEA: (1'S, 1R,2S)-2-(1'-phenylethylamino)cyclohexylamino, CCA: cis-2-aminocyclohexylamino, ACA:(1R,2S)-2-aminocyclohexylamino. Sal: salt (blank space: free form; HCl: hydrochloride), Dat: physicochemical data (F: FAB-MS (M+H)$^+$; FN: FAB-MS (M−H)$^−$; M: melting point (° C.); A: specific rotation $[\alpha]_D$ (MeOH)). Also, a compound in which $R^2$ is 3,4-(CH—)$_4$=(CH-CH=CH) represents a 2-naphthyl group together with the adjacent benzene ring, and OCH$_2$O represents methylenedioxy group.

TABLE 1

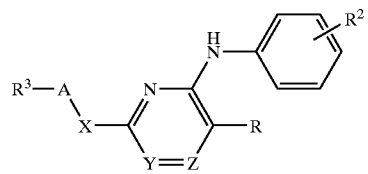

| Rex | R³-A-X- | R² | Y | Z | R | Dat |
|---|---|---|---|---|---|---|
| 4 | Cl | 3-Me | CH | N | CONH₂ | F: 263 |
| 5 | BCA | 3-Br | N | C—OH | CONH₂ | F: 522 |
| 6 | BCA | 3-Me | N | C—O(2-Cl—Ph) | CN | F: 549 |
| 7 | CCA | 3-Me | N | C—OBn | CONH₂ | F: 447 |
| 8 | Cl | 3-MeO | CH | N | CONH₂ | F: 279 |
| 9 | Cl | 3-PhO | CH | N | CONH₂ | FN: 339 |
| 10 | Cl | 3,5-MeO | CH | N | CONH₂ | F: 309 |
| 11 | Cl | 4-MeS | CH | N | CONH₂ | F: 294 |
| 12 | Cl | 3-Me | CH | CH | CONH₂ | F: 262 |
| 13 | Cl | 3-CF₃ | CH | CH | CONH₂ | F: 316 |
| 14 | Cl | 3-Et | CH | CH | CONH₂ | F: 276 |
| 15 | Cl | 3,5-Me | CH | CH | CONH₂ | F: 276 |
| 16 | Cl | 3-Me | N | C—Cl | CN | F: 279 |
| 17 | Cl | 3-Br | N | C—Cl | CN | F: 344 |
| 18 | BocHN-CH₂CH₂-NH- | 3-Me | N | C—Cl | CN | FN: 401 |
| 19 | BCA | 3-Me | N | C—Cl | CN | F: 457 |
| 20 | BCA | 3-Br | N | C—Cl | CN | F: 522 |
| 21 | PEA | 3-Me | CH | N | CONH₂ | F: 445 |
| 22 | PEA | 3-MeO | CH | N | CONH₂ | F: 461 |
| 23 | PEA | 3,5-MeO | CH | N | CONH₂ | F: 491 |
| 24 | BocHN-CH₂CH₂-NH- | 3-Me | N | C—OH | CONH₂ | F: 403 |
| 25 | BCA | 3-Me | N | C—O(2-Cl—Ph) | CONH₂ | F: 567 |

TABLE 2

| Ex | R³-A-X- | R² | Y | Z | Sal | Dat |
|---|---|---|---|---|---|---|
| 1 | CCA | 3-Me | CH | CH | HCl | F: 340 |
| 2 | CCA | 3-Me | CH | N | | F: 341; M: 221–224 |
| 3 | CCA | 3-Me | N | C—OH | | F: 357; M: 280–285 |
| 4 | CCA | 3-Br | N | C—OH | HCl | F: 421, 423 |
| 5 | H₂N–CH₂CH₂–NH– | 3-CF₃ | CH | CH | | F: 340; M: 172–176 |
| 6 | H₂N–CH₂CH₂–NH– | 3-Et | CH | CH | | F: 300; M: 134–136 |
| 7 | CCA | 3,5-Me | CH | CH | HCl | F: 354 |
| 8 | CCA | 3-MeO | CH | N | | F: 357; M: 194–197 |
| 9 | CCA | 3-PhO | CH | N | | F: 419 |
| 10 | CCA | 3,5-MeO | CH | N | | F: 387; M: 210–212 |
| 11 | CCA | 4-MeS | CH | N | | F: 373 |
| 12 | ACA | 3-Me | CH | N | | F: 341; A: +78° (C = 0.1) |
| 13 | ACA | 3-MeO | CH | N | | F: 357; A: +89° (C = 0.2) |
| 14 | ACA | 3,5-MeO | CH | N | | F: 387; A: +82° (C = 0.2) |
| 15 | CCA | 3-Me | N | C—O(2-Cl—Ph) | | F: 467 |
| 16 | H₂N–CH₂CH₂–N(Me)– | 3-Me | N | C—OH | | F: 303 |

TABLE 3

| Cmpd | R² |
|---|---|
| 1 | 2-Br |
| 2 | 3-Br |
| 3 | 4-Br |
| 4 | 2-Cl |
| 5 | 3-Cl |
| 6 | 4-Cl |
| 7 | 2-HOCH₂ |
| 8 | 3-HOCH₂ |
| 9 | 4-HOCH₂ |
| 10 | 2-H₂N |
| 11 | 3-H₂N |
| 12 | 4-H₂N |
| 13 | 2-Ac |
| 14 | 3-Ac |
| 15 | 4-Ac |
| 16 | 2-MeS |
| 17 | 3-MeS |
| 18 | 4-MeS |
| 19 | 2-PhO |
| 20 | 3-PhO |
| 21 | 4-PhO |
| 22 | 2-MeO |
| 23 | 3-MeO |
| 24 | 4-MeO |
| 25 | 2-Me |
| 26 | 3-Me |
| 27 | 4-Me |
| 28 | 2-Bu |
| 29 | 3-Bu |
| 30 | 4-Bu |
| 31 | 3,5-Cl |
| 32 | 3,5-MeO |
| 33 | 3,5-Me |
| 34 | 2,3-OCH₂O |
| 35 | 3,4-OCH₂O |
| 36 | 3,4-(CH=CH—CH=CH) |

TABLE 4

Structure: cyclohexane-1,2-diamine (H₂N, NH) linked to pyridine bearing CONH₂ and NH-phenyl-R²

| Cmpd | R² |
|---|---|
| 37 | 2-Br |
| 38 | 3-Br |
| 39 | 4-Br |
| 40 | 2-Cl |
| 41 | 3-Cl |
| 42 | 4-Cl |
| 43 | 2-HOCH₂ |
| 44 | 3-HOCH₂ |
| 45 | 4-HOCH₂ |
| 46 | 2-H₂N |
| 47 | 3-H₂N |
| 48 | 4-H₂N |
| 49 | 2-Ac |
| 50 | 3-Ac |
| 51 | 4-Ac |
| 52 | 2-MeS |
| 53 | 3-MeS |
| 54 | 4-MeS |
| 55 | 2-PhO |
| 56 | 3-PhO |
| 57 | 4-PhO |
| 58 | 2-MeO |
| 59 | 3-MeO |
| 60 | 4-MeO |
| 61 | 2-Me |
| 62 | 4-Me |
| 63 | 2-Et |
| 64 | 3-Et |
| 65 | 4-Et |
| 66 | 3-Pr |
| 67 | 3-Bu |
| 68 | 3,5-Cl |
| 69 | 3,5-MeO |
| 70 | 2,3-OCH₂O |
| 71 | 3,4-OCH₂O |
| 72 | 3,4-(CH=CH—CH=CH) |

TABLE 5

Structure: R³-A-X- linked to pyridine bearing CONH₂ and NH-phenyl-R²

| Cmpd | R³-A-X- | R² |
|---|---|---|
| 73 | 4-(aminomethyl)-N-methylanilino (H₂N-CH₂-C₆H₄-NH-) | 3-Me |
| 74 | " | 3-Br |
| 75 | " | 3-MeO |
| 76 | HONH-C(O)-CH₂-C₆H₄-NH(Me)- | 3-Me |
| 77 | " | 3-Br |
| 78 | " | 3-MeO |
| 79 | MeONH-C(O)-CH₂-C₆H₄-NH(Me)- | 3-Me |
| 80 | " | 3-Br |
| 81 | " | 3-MeO |
| 82 | 2-(aminomethyl)-N-methylanilino | 3-Me |
| 83 | " | 3-Br |
| 84 | " | 3-MeO |
| 85 | 5-carboxy-2-(methylamino)pyridinyl (HOOC-pyridine-NH-) | 3-Me |
| 86 | " | 3-Br |
| 87 | " | 3-MeO |
| 88 | 2-amino-cycloheptyl-NH(Me)- | 3-Me |
| 89 | " | 3-Br |
| 90 | " | 3-MeO |
| 91 | H₂N-(CH₂)₃-NH(Me)- | 3-Me |
| 92 | " | 3-Br |
| 93 | " | 3-MeO |
| 94 | (5-methyl-2-oxo-1,3-dioxol-4-yl)methyl-OC(O)-NH-CH₂CH₂-NH(Me)- | 3-Me |
| 95 | " | 3-Br |
| 96 | " | 3-MeO |

TABLE 5-continued

Structure: R³-A-X- attached to pyridine with NH-phenyl(R²) and CONH₂ group

| Cmpd | R³-A-X- | R² |
|------|---------|-----|
| 97 | 4-(HOOC-)-C₆H₄-NH- | 3-Me |
| 98 | " | 3-Br |
| 99 | " | 3-MeO |
| 100 | 4-(H₂NOC-)-C₆H₄-NH- | 3-Me |
| 101 | " | 3-Br |
| 102 | " | 3-MeO |
| 103 | 4-(MeNHOC-)-C₆H₄-NH- | 3-Me |
| 104 | " | 3-Br |
| 105 | " | 3-MeO |
| 106 | 5-(H₂NCH₂)-pyridin-2-yl-NH- | 3-Me |
| 107 | " | 3-Br |
| 108 | " | 3-MeO |
| 109 | 2-aminocyclopentyl-NH- | 3-Me |
| 110 | " | 3-Br |
| 111 | " | 3-MeO |
| 112 | 3-aminocyclohexyl-NH- | 3-Me |
| 113 | " | 3-Br |
| 114 | " | 3-MeO |
| 115 | H₂N-(CH₂)₄-NH- | 3-Me |
| 116 | " | 3-Br |
| 117 | " | 3-MeO |
| 118 | 2-[(2-acetoxyphenyl)-CH=CH-C(O)-NH-]cyclohexyl-NH- | 3-Me |
| 119 | " | 3-Br |
| 120 | " | 3-MeO |

TABLE 6

Structure: 1,2,4-triazine with (2-aminocyclohexyl)amino, NH-phenyl(R²), and CONH₂ substituents

| Cmpd | R² |
|------|-----|
| 121 | 2-Br |
| 122 | 3-Br |
| 123 | 4-Br |
| 124 | 2-Cl |
| 125 | 3-Cl |
| 126 | 4-Cl |
| 127 | 2-HOCH₂ |
| 128 | 3-HOCH₂ |
| 129 | 4-HOCH₂ |
| 130 | 2-H₂N |
| 131 | 3-H₂N |
| 132 | 4-H₂N |
| 133 | 2-Ac |
| 134 | 3-Ac |
| 135 | 4-Ac |
| 136 | 2-MeS |
| 137 | 3-MeS |
| 138 | 4-MeS |
| 139 | 2-PhO |
| 140 | 3-PhO |
| 141 | 4-PhO |
| 142 | 2-MeO |
| 143 | 3-MeO |
| 144 | 4-MeO |
| 145 | 2-Me |
| 146 | 3-Me |
| 147 | 4-Me |
| 148 | 2-Et |
| 149 | 3-Et |
| 150 | 4-Et |
| 151 | 3,5-Cl |
| 152 | 3,5-MeO |
| 153 | 3,5-Me |
| 154 | 2,3-OCH₂O |
| 155 | 3,4-OCH₂O |
| 156 | 3,4-(CH=CH—CH=CH) |

TABLE 7

| Cmpd | R² |
|---|---|
| 157 | 2-Br |
| 158 | 3-Br |
| 159 | 4-Br |
| 160 | 2-Cl |
| 161 | 3-Cl |
| 162 | 4-Cl |
| 163 | 2-F |
| 164 | 3-F |
| 165 | 4-F |
| 166 | 2-HOCH₂ |
| 167 | 3-HOCH₂ |
| 168 | 4-HOCH₂ |
| 169 | 2-H₂N |
| 170 | 3-H₂N |
| 171 | 4-H₂N |
| 172 | 2-Ac |
| 173 | 3-Ac |
| 174 | 4-Ac |
| 175 | 2-MeS |
| 176 | 3-MeS |
| 177 | 4-MeS |
| 178 | 2-PhO |
| 179 | 3-PhO |
| 180 | 4-PhO |
| 181 | 2-MeO |
| 182 | 4-MeO |
| 183 | 2-Me |
| 184 | 4-Me |
| 185 | 2-Et |
| 186 | 3-Et |
| 187 | 4-Et |
| 188 | 3,5-MeO |
| 189 | 3,5-Me |
| 190 | 2,3-OCH₂O |
| 191 | 3,4-OCH₂O |
| 192 | 3,4-(CH=CH—CH=CH) |

TABLE 8

| Cmpd | R³-A-X- | R² |
|---|---|---|
| 193 | H₂N-CH₂-C₆H₄-NH- (para) | 3-Me |
| 194 | | 3-Br |
| 195 | | 3-MeO |
| 196 | HONH-C(O)-CH₂-C₆H₄-NH- (para) | 3-Me |
| 197 | | 3-Br |
| 198 | | 3-MeO |
| 199 | MeONH-C(O)-CH₂-C₆H₄-NH- (para) | 3-Me |
| 200 | | 3-Br |
| 201 | | 3-MeO |
| 202 | 2-(aminomethyl)-C₆H₄-NH(Me)- | 3-Me |
| 203 | | 3-Br |
| 204 | | 3-MeO |
| 205 | 6-(methylamino)nicotinic acid | 3-Me |
| 206 | | 3-Br |
| 207 | | 3-MeO |
| 208 | 2-amino-cycloheptyl-NH- | 3-Me |
| 209 | | 3-Br |
| 210 | | 3-MeO |
| 211 | H₂N-(CH₂)₃-NH- | 3-Me |
| 212 | | 3-Br |
| 213 | | 3-MeO |
| 214 | (5-methyl-2-oxo-1,3-dioxol-4-yl)methyl carbamate linker | 3-Me |
| 215 | | 3-Br |
| 216 | | 3-MeO |

TABLE 8-continued

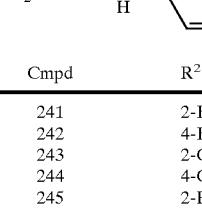

| Cmpd | R³-A-X- | R² |
|------|---------|-----|
| 217 | 4-(HOOC)C₆H₄-NH- | 3-Me |
| 218 | | 3-Br |
| 219 | | 3-MeO |
| 220 | 4-(H₂NOC)C₆H₄-NH- | 3-Me |
| 221 | | 3-Br |
| 222 | | 3-MeO |
| 223 | 4-(MeHNOC)C₆H₄-NH- | 3-Me |
| 224 | | 3-Br |
| 225 | | 3-MeO |
| 226 | 5-(H₂NCH₂)-2-pyridyl-NH- | 3-Me |
| 227 | | 3-Br |
| 228 | | 3-MeO |
| 229 | 2-aminocyclopentyl-NH- | 3-Me |
| 230 | | 3-Br |
| 231 | | 3-MeO |
| 232 | 3-aminocyclohexyl-NH- | 3-Me |
| 233 | | 3-Br |
| 234 | | 3-MeO |
| 235 | H₂N(CH₂)₄-NH- | 3-Me |
| 236 | | 3-Br |
| 237 | | 3-MeO |

TABLE 8-continued

| Cmpd | R³-A-X- | R² |
|------|---------|-----|
| 238 | 2-aminocyclohexyl-NH-C(O)-CH=CH-(2-AcO-C₆H₄)- | 3-Me |
| 239 | | 3-Br |
| 240 | | 3-MeO |

TABLE 9

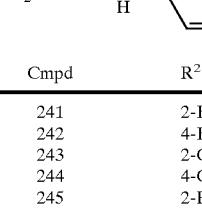

| Cmpd | R² |
|------|-----|
| 241 | 2-Br |
| 242 | 4-Br |
| 243 | 2-Cl |
| 244 | 4-Cl |
| 245 | 2-F |
| 246 | 4-F |
| 247 | 2-HOCH₂ |
| 248 | 3-HOCH₂ |
| 249 | 4-HOCH₂ |
| 250 | 2-H₂N |
| 251 | 3-H₂N |
| 252 | 4-H₂N |
| 253 | 2-Ac |
| 254 | 3-Ac |
| 255 | 4-Ac |
| 256 | 2-MeS |
| 257 | 3-MeS |
| 258 | 4-MeS |
| 259 | 2-PhO |
| 260 | 4-PhO |
| 261 | 2-MeO |
| 262 | 4-MeO |
| 263 | 2-Et |
| 264 | 4-Et |
| 265 | 2-NO₂ |
| 266 | 3-NO₂ |
| 267 | 4-NO₂ |
| 268 | 2-CN |
| 269 | 3-CN |
| 270 | 4-CN |
| 271 | 3,5-Br |
| 272 | 3,5-Cl |
| 273 | 3,5-F |
| 274 | 2,3-OCH₂O |
| 275 | 3,4-OCH₂O |
| 276 | 3,4-(CH=CH—CH=CH) |

TABLE 10

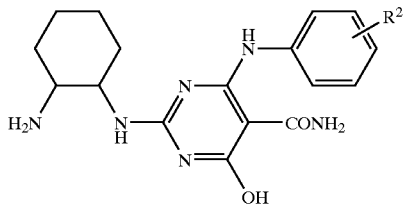

| Cmpd | R² |
|---|---|
| 277 | 2-F |
| 278 | 3-F |
| 279 | 4-F |
| 280 | 2-Cl |
| 281 | 3-Cl |
| 282 | 4-Cl |
| 283 | 2-HOCH₂ |
| 284 | 3-HOCH₂ |
| 285 | 4-HOCH₂ |
| 286 | 2-H₂N |
| 287 | 3-H₂N |
| 288 | 4-H₂N |
| 289 | 2-Ac |
| 290 | 3-Ac |
| 291 | 4-Ac |
| 292 | 2-MeS |
| 293 | 3-MeS |
| 294 | 4-MeS |
| 295 | 2-PhO |
| 296 | 3-PhO |
| 297 | 4-PhO |
| 298 | 2-MeO |
| 299 | 3-MeO |
| 300 | 4-MeO |
| 301 | 2-Et |
| 302 | 3-Et |
| 303 | 4-Et |
| 304 | 2-Bu |
| 305 | 3-Bu |
| 306 | 4-Bu |
| 307 | 3,5-Cl |
| 308 | 3,5-MeO |
| 309 | 3,5-Me |

TABLE 10-continued

| Cmpd | R² |
|---|---|
| 310 | 2,3-OCH₂O |
| 311 | 3,4-OCH₂O |
| 312 | 3,4-(CH=CH—CH=CH) |

TABLE 11

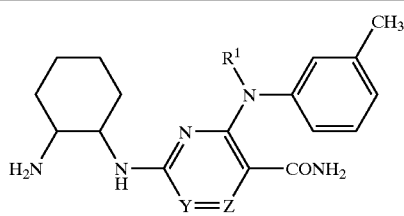

| Cmpd | R¹ | Y | Z |
|---|---|---|---|
| 313 | Me | CH | CH |
| 314 | Ac | | |
| 315 | MeSO₂ | | |
| 316 | Me | CH | N |
| 317 | Ac | | |
| 318 | MeSO₂ | | |
| 319 | H | N | C(NHPh) |
| 320 | | | C(NMePh) |
| 321 | | | C—Me |
| 322 | | | C—Ph |
| 323 | | | C—OMe |

---

What is claimed is:

1. A heterocyclecarboxamide derivative represented by the general formula (I) or a pharmaceutically acceptable salt,

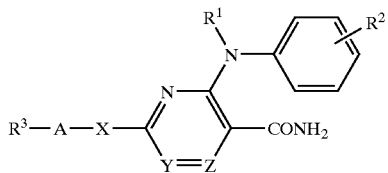

wherein the symbols in the formula have the following meanings:

A: a lower alkylene which may have substituent(s), an arylene which may have substituent(s), a heteroarylene comprising a five to six-membered momocyclic group having from one to four hetero atoms selected from O, S, and N, which may have substituent(s), or a cycloalkylene which may have substituent(s);

X: $NR^4$;

Y=Z: $C(R^7)$=N;

$R^1$, $R^4$: H, a lower alkyl, —CO-lower alkyl, or —$SO_2$-lower alkyl;

$R^2$: H, alower alkyl, a halogen, a lower alkyl substituted by halogen(s), —O-lower alkyl, —S-lower alkyl, —O-aryl, —O-lower alkylene-aryl, —S-lower alkylene-aryl, nitro, cyano, $OCH_2O$, or —(CH=CH—CH=CH)—;

$R^3$: —$CO_2H$, —$CO_2$-lower alkyl, -lower alkylene-$CO_2H$, -lower alkylene-$CO_2$-lower alkyl, -CONHOH, —CONHO-lower alkyl, -lower alkylene-CONHOH, -lower alkylene-CONHO-lower alkyl, —$NH_2$, —($NH_2$ in a prodrug form), -lower alkylene-$NH_2$, or -lower alkylene-($NH_2$ in a prodrug form);

$R^7$: H, a lower alkyl, —OH, —O-lower alkyl, —O-aryl which may have substituent(s), —O-lower alkylene-aryl which may have substituent(s), —$NR^1$-aryl which may have substituent(s), —CO-lower alkyl, or -aryl group which may have substituent(s).

2. The compound or a pharmaceutically acceptable salt according to claim 1, wherein X is $NR^4$ and A is a lower alkylene or cycloalkylene.

3. The compound or a pharmaceutically acceptable salt according to claim 1, wherein the compound is selected from 5-(cis-2-aminocyclohexylamino)-3-(3-methoxyanilino)pyrazine-2-carboxamide, 5-(cis-2-aminocyclohexylamino)-3-(3-phenoxyanilino)pyrazine-2-carboxamide, 5-(cis-2-aminocyclohexylamino)-3-(4-methylsulfanylanilino)pyrazine-2-carboxamide, 5-(cis-2-aminocyclohexylamino)-3-(3,5-dimethoxyanilino)pyrazine-2-carboxamide.

4. A pharmaceutical composition which comprises the compound according to claim 1 or a pharmaceutically acceptable salt and a pharmaceutically acceptable carrier.

5. A pharmaceutical composition which comprises the compound according to claim 1 which is a Syk inhibitor or a pharmaceutically acceptable salt and a pharmaceutically acceptable carrier.

* * * * *

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Band 3 peptide
<221> NAME/KEY: MOD_RES
<222> LOCATION: (1)..(18)
<223> OTHER INFORMATION: PHOSPHORYLATION

<400> SEQUENCE: 1

Met Glu Glu Leu Gln Asp Asp Tyr Glu Asp Met Met Glu Glu Asn Leu
1               5                   10                  15

Glu Gln